United States Patent [19]

Phillipps et al.

[11] 4,093,721

[45] June 6, 1978

[54] PHARMACEUTICAL COMPOSITIONS OF 6α,9α-DIFLUORO-ANDROST-4-ENE-17β-CARBOXYLATES AND DERIVATIVES THEREOF

[75] Inventors: Gordon H. Phillipps, Wembley; Brian M. Bain, Chalfont St. Peter, both of England

[73] Assignee: Glaxo Laboratories Limited, Greenford, England

[21] Appl. No.: 757,325

[22] Filed: Jan. 6, 1977

Related U.S. Application Data

[63] Continuation of Ser. No. 609,043, Aug. 29, 1975, abandoned.

[30] Foreign Application Priority Data

Aug. 30, 1974 United Kingdom ............... 38090/74

[51] Int. Cl.$^2$ .............................................. A61K 31/56
[52] U.S. Cl. ................................... 424/243; 260/397.1
[58] Field of Search ....................... 260/397.1; 424/243

[56] References Cited

U.S. PATENT DOCUMENTS

| | | | |
|---|---|---|---|
| 3,636,010 | 1/1972 | Anner et al. | 260/397.1 |
| 3,856,828 | 12/1974 | Phillipps et al. | 260/397.1 |

*Primary Examiner*—Elbert L. Roberts
*Attorney, Agent, or Firm*—Bacon & Thomas

[57] ABSTRACT

The specification describes anti-inflammatory steroids having the following formula

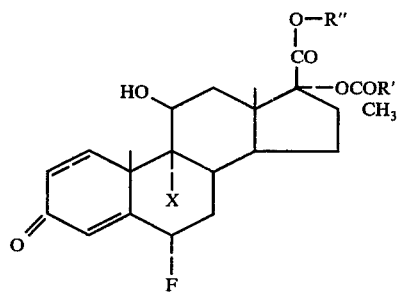

wherein X represents a hydrogen or fluorine atom, R' represents a methyl, ethyl, n-propyl or iso-propyl group, R" represents a methyl, chloromethyl, fluoromethyl, bromomethyl or 2-fluoroethyl group and represents a single or double bond. The specification describes processes for preparing such compounds as well as pharmaceutical compositions containing the compounds.

13 Claims, No Drawings

PHARMACEUTICAL COMPOSITIONS OF 6α,9α-DIFLUORO-ANDROST-4-ENE-17β-CARBOXYLATES AND DERIVATIVES THEREOF

This is a continuation of application Ser. No. 609,043, filed Aug. 29, 1975, now abandoned.

The present invention relates to novel anti-inflammatory steroids of the androstane series.

U.S. Pat. No. 3,636,010 broadly discloses a class of androstane steroids having the general formula

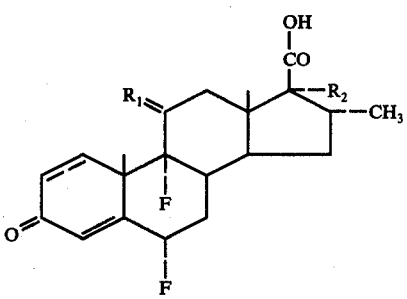

(wherein R₁ represents either a β-hydroxy group together with a hydrogen atom, or an oxo group, R₂ represents a hydrogen atom or a free or esterified hydroxy group and $=$ represents a single or double bond) together with carboxylic acid metal salts and esters thereof. These steroids are described in the Patent as having a pronounced anti-inflammatory action as well as a strong thymolytic action after systemic administration. The said Patent suggests that Δ¹,⁴-16α-methyl-6α,9α-difluoro-11β,17α-dihydroxy-3-oxo-androstadiene-17β-carboxylic acid methyl ester is the preferred compound according to the invention on account of its good anti-inflammatory activity. It should be noted that this compound is a 17α-hydroxy compound and that the remaining compounds specifically described in the Patent (including the Examples) likewise possess a free hydroxy group in the 17α-position. Indeed, the Patent does not specifically describe any androstane compounds of the above general formula having an esterified hydroxy group in the 17α-position.

We have now discovered that a narrow class of new androstane compounds, some of which fall within the scope of the above general formula, having certain ester groups (as hereinafter defined) in the 17α-position, possess greatly superior anti-inflammatory activities, particularly on topical application, to those of the 17α-hydroxy compounds disclosed in the above Patent. We have further discovered that the new class of androstane compounds referred to above possess, in general, a good ratio of topical anti-inflammatory activity to undesired glucocorticoid activity as measured for example in the thymus involution test on the mouse.

The new class of androstane compounds can be represented by the general formula

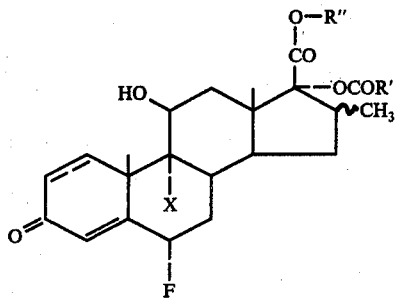

wherein X represents a hydrogen or fluorine atom, R' represents a methyl, ethyl, n-propyl or iso-propyl group, R" represents a methyl, chloromethyl, fluoromethyl, bromomethyl or 2-fluoroethyl group and $=$ represents a single or double bond. In the above general formula I, R' preferably represents an ethyl group. R" preferably represents a methyl, chloromethyl or fluoromethyl group.

Preferred compounds according to the present invention on account of their high topical anti-inflammatory activity are methyl 6α,9α-difluoro-11β-hydroxy-16α methyl-3-oxo-17α-propionyloxyandrosta-1,4-diene-17β-carboxylate and fluoromethyl-6α,9α-difluoro-11β-hydroxy-16β-methyl-3-oxo-17α-propionyloxy-androst-4-ene-17β-carboxylate.

The new compounds described above may be prepared in a number of ways, for example from appropriate 6α-fluoro compounds or by the introduction of a fluorine substituent into corresponding 6-unsubstituted compounds.

Thus, for example, the new compounds may be prepared by esterifying a corresponding 17α-acyloxy 17β-carboxylic acid (or functional equivalent thereof) or 17α-hydroxy 17β-carboxylate to produce the desired compound.

Thus, the parent 17α-acyloxy-17β-carboxylic acid of compounds of formula I may be esterified, to provide 17β-carboxylate esters according to the invention. For example, in order to prepare a methyl ester the 17β-carboxylic acid may be reacted with diazomethane, the reaction being preferably effected in a solvent medium, e.g. ether, tetrahydrofuran or methanol, and at a low temperature, preferably at −5° to +30° C. Alternatively, the 17β-carboxylic acid may be reacted with O-methyl N,N'-dicyclohexyl-isourea, preferably in an aprotic solvent such as ethyl acetate, and advantageously at a temperature of 25°–100° C. Alternatively, a salt of the parent 17β-carboxylic acid for example, an alkali metal e.g. lithium, sodium or potassium, salt or a quaternary ammonium, e.g. triethylammonium or tetrabutylammonium, salt may be reacted with a methylating agent, for example, a methyl halide e.g. the iodide, or a sulphonyloxy compound including dimethylsulphate, preferably in a polar solvent medium such as a ketone, e.g. acetone or methylethyl ketone or an amide solvent e.g. dimethylformamide or hexamethylphosphoramide conveniently at a temperature in the range 15°–100° C.

For the preparation of those compounds of formula I wherein R" represents a chloromethyl, fluoromethyl, bromomethyl or 2-fluoroethyl group, the esterification of the 17β-carboxyl group can be carried out in an analogous manner to that described above for the preparation of the methyl ester. Thus, for example, such esters may be prepared by reacting a salt of the parent 17β-carboxylic acid with a compound R″Y where Y is an appropriate displaceable substituent e.g. a halogen atom, preferably iodine. This method is particularly applicable to the preparation of those compounds of formula I wherein R″ represents a chloromethyl group, the said halo compound in this case being iodochloromethane. The salt of the parent 17β-carboxylic acid employed in this process may be one specifically mentioned above in relation to the preparation of the methyl 17β-carboxylate compounds of the invention.

Alternatively, the parent 17α-hydroxy-17β-carboxylates corresponding to compounds of formula I may be subjected to esterification of the 17α-hydroxyl group; such 17α-hydroxy-17β-carboxylates may be prepared by esterifying the corresponding 17α-hydroxy-17β-carboxylic acids by the methods described above.

The esterification of the 17α-hydroxy group in the preparation of the new androstance compounds may, if desired, be effected by conventional techniques, e.g. by reacting the parent 17α-hydroxy compound with a mixed anhydride of the required carboxylic acid, which may, for example, be generated in situ by reacting the carboxylic acid with an appropriate anhydride such as trifluoroacetic anhydride, preferably in the presence of an acid catalyst, e.g. p-toluene-sulphonic acid or sulphosalicylic acid. Alternatively, the mixed anhydride may be generated in situ by reaction of a symmetrical anhydride of the required acid with an appropriate further acid, e.g. trifluoroacetic acid.

The reaction is advantageously effected in an organic solvent medium such as benzene, methylene chloride or an excess of the carboxylic acid employed, the reaction being conveniently effected at a temperature of 20°–100° C.

Alternatively, the 17α-hydroxy group may be esterified by reaction of the parent 17α-hydroxy compound with the appropriate acid anhydride or acid chloride, if desired, in the presence of non-hydroxylic solvents, e.g. chloroform, methylene chloride or benzene, and preferably in the presence of a strong acid catalyst, e.g. perchloric acid, p-toluene sulphonic acid or a strongly acidic cation exchange resin, e.g. Amberlite IR 120, the reaction being conveniently effected at a temperature of 25° to 100° C.

For the preparation of the 17α-esters of the 17β-carboxylic acids which may be employed in the preparation of the compounds according to the invention, it is often preferred to treat the parent 17α-hydroxy 17β-carboxylic acid with the appropriate carboxylic acid anhydride, if desired in the presence of a base such as potassium carbonate. Any mixed anhydride formed may be solvolysed under acidic (e.g. aqueous acetic acid) or basic (e.g. aqueous pyridine or diethylamine-/acetone) conditions. Alternatively, the parent 17α-hydroxy 17β-carboxylic acid may be treated with the appropriate carboxylic acid chloride, preferably in a solvent such as an halogenated hydrocarbon e.g. methylene chloride, and advantageously in the presence of a base such as triethylamine, preferably at a low temperature e.g. 0° C.

Those compounds of formula I wherein R″ represents a chloromethyl, fluoromethyl, bromomethyl or 2-fluoroethyl group may also be prepared by reacting a compound of formula

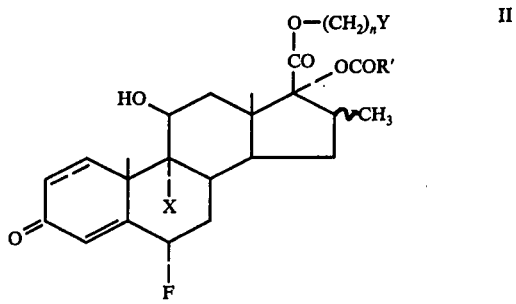

(wherein X, R′ and ═ are as defined above, n is 1 or 2 and Y represents a displaceable substituent) with a compound serving to replace the group Y by a fluorine, chlorine or bromine atom when n is 1 or by a fluorine atom when n is 2. Y may thus, for example, be a chlorine, bromine or iodine atom.

In accordance with the last-mentioned process fluoromethyl or 2-fluoroethyl 17β-carboxylate compounds of formula I may be prepared from the corresponding chloro-, bromo- or iodo-methyl or -ethyl compounds by reaction with an appropriate fluoride, e.g. silver monofluoride or silver difluoride, conveniently in a solvent, for example acetonitrile.

The new 2-fluoroethyl 17β-carboxylate compounds of formula I can also be prepared from a corresponding sulphonyloxyethyl, e.g. mesyloxyethyl, compound of formula II by reaction with an appropriate alkali metal, alkaline earth metal or quaternary ammonium fluoride conveniently in a solvent medium, e.g. acetone, dimethyl formamide, hexamethylphosphoramide or ethanol. The sulphonyloxy ethyl compound may be prepared from a corresponding 2-hydroxyethyl compound produced, for example, by reaction of a 17β-carboxylic acid salt with an appropriate halohydrin.

The compounds of general formula II as well as the parent 17β-carboxylic acids referred to above may be prepared for example in accordance with the general procedures described in Belgian Pat. Nos. 778285 and 802481.

The $\Delta^4$ compounds according to the invention can conveniently be prepared by partial reduction of the corresponding $\Delta^{1,4}$ compound, for example, by hydrogenation using a palladium catalyst, conveniently in a solvent e.g. ethyl acetate or by homogeneous hydrogenation using for example tris(triphenylphosphine)rhodium chloride, conveniently in a solvent such as benzene, or by exchange hydrogenation using for example cyclohexene in the presence of a palladium catalyst in a solvent e.g. ethanol, preferably under reflux. This reduction may be carried out on a haloalkyl ester where this is sufficiently stable in such a reaction or may be effected at an earlier stage.

The new compounds can also be prepared, as indicated above, from the corresponding 6-unsubstituted compounds, e.g. by preparation of a corresponding 3-enol ester or ether followed by reaction with an electrophilic fluorinating agent such as perchloryl fluoride and subsequent hydrolysis to yield the corresponding 6β-fluoro compound. Where no 1,2-double bond is present, treatment with a strong acid such as hydrogen chloride or more preferably hydrogen bromide effects epimerisation to form the desired 6α-fluoro compound. The epimerisation is preferably effected in a non-aqueous solvent medium, dioxan being particularly preferred; other solvents which may be used include tetrahydrofuran, ester solvents such as ethyl acetate, ketone solvents and amide solvents such as dimethylacetamide or dimethylformamide. The epimerisation is also advantageously effected in the presence of a carboxylic acid such as acetic acid, especially when hydrogen bromide is employed. In the case of $\Delta^{1,4}$-compounds, it is necessary to hydrogenate the 1,2-double bond, e.g. by catalytic hydrogenation, effect the epimerisation and reintroduce the 1,2-double bond by dehydrogenation, normally under neutral or mildly acidic conditions e.g. using dichlorodicyanoquinone or chloranil. Suitable solvents for this reaction include hydrocarbon solvents, e.g. benzene, esters e.g. ethyl acetate, and ether solvents, e.g. dioxan.

As is well known to those skilled in the art it may frequently be convenient to elaborate the desired substituents in the 17α- and 17β-positions at an intermediate stage of the preparation of the desired final compound, one or more other substituents (or unsaturation) being introduced at a later stage. Instances where the desired substituents may be introduced before final elaboration of the remainder of the desired androstane molecule include for example preparing $\Delta^{9(11)}$ or Ring A saturated compounds having the desired 17α-acyloxy and 17β-carboxylate ester groups, completion of the elaboration of Rings A, B and C then being effected in conventional manner.

There are also provided pharmaceutical compositions for use in anti-inflammatory therapy, comprising at least one androstane compound of formula I (as defined above), together with one or more pharmaceutical carriers or excipients. Such compositions may be in forms adapted for topical or internal administration.

The active androstane compounds may be formulated into preparations suitable for topical administration with the aid of a topical vehicle therefor. Example of various types of preparation for topical administration, include ointments, lotions, creams, powders, drops, (e.g. eye or ear drops), sprays, (e.g. for the nose or throat), suppositories, retention enemas, chewable or suckable tablets or pellets (e.g. for the treatment of aphthous ulcers) and aerosols. Ointments and creams may for example, be formulated with an aqueous or oily base with the addition of suitable thickening and/or gelling agents and/or glycols. Such a base may thus, for example, include water and/or an oil such as liquid paraffin or a vegetable oil such as arachis oil or castor oil, or a glycolic solvent such as propylene glycol or 1,3-butane-diol. Thickening agents which may be used according to the nature of the base include soft paraffin, aluminium stearate, cetostearyl alcohol, polyethylene glycols, woolfat, hydrogenated lanolin and beeswax and/or glyceryl monostearate and/or non-ionic emulsifying agents.

The solubility of the steroid in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following namely, emulsifying agents, dispersing agents, suspending agents, thickening agents, colouring agents, perfumes and solvents.

Powders may be formed with the aid of any suitable powder base e.g. talc, lactose or starch. Drops may be formulated with an aqueous base also comprising one or more dispersing agents, suspending agents or solubilising agents etc.

Spray compositions may for example be formulated as aerosols with the use of a suitable propellant, e.g. dichlorodifluoromethane or trichlorofluoromethane.

The proportion of active androstane compound in the topical compositions according to the invention depends on the precise type of formulations to be prepared but will generally be within the range of from 0.0001 to 5.0% by weight. Generally however for most types of preparations advantageously the proportion used will be within the range of from 0.001 to 0.5% and preferably 0.01 to 0.25%.

Topical preparations may be administered by one or more applications per day to the affected area; over skin areas occlusive dressings may often be used with advantage.

For internal administration the new compounds according to the invention may, for example, be formulated for oral, parenteral or rectal administration. For oral administration syrups, elixirs, powders and granules may be used which may be formulated in conventional manner. Dosage unit forms are however preferred as described below.

For parenteral administration the compounds may be presented in sterile aqueous or oily vehicles, suitable oily vehicles including arachis oil, olive oil etc.

Preferred forms of preparations for internal administration are dosage unit forms i.e. presentations in unitary form in which each unit contains a desired dose of the active steroid. Such dosage unit forms contain from 0.05 to 2.0 mg, preferably from 0.25 to 1.0 mg of the active steroid. For oral administration suitable dosage unit forms include tablets, coated tablets and capsules. For parenteral administration dosage unit forms include sealed ampoules or vials each containing a desired dose of the steroid. Suppositories, which may be prepared for example with conventional commercial suppository bases, provide a dosage unit form for rectal administration. Sterile tablets or pellet implants may also be used, e.g. where slow systemic absorption is desired.

The compounds according to the invention may in general be given by internal administration in cases where systemic adreno-cortical therapy is indicated.

In general terms preparations for internal administration may contain from 0.01 to 5.0% of active ingredient depending upon the type of preparation involved. The daily dose may vary from 0.5 to 10.0 mg. dependent on the condition being treated and the duration of treatment desired.

The compositions according the invention may also include one or more preservatives or bacteriostatic agents e.g. methyl hydroxy benzoate, propyl hydroxy benzoate, chlorocresol or benzalkonium chlorides. The compositions according to the invention may also contain, other active ingredients such as antimicrobial agents, particularly antibiotics such as neomycin.

The following Examples illustrate the present invention. In the Examples (and also the Preparations), the ultra violet spectra are in ethanol. Melting points were determined on a Kofler block, and are uncorrected. Preparative thin layer chromatography (P.L.C.) was carried out on silica; following P.L.C., products were isolated by elution with ethyl acetate.

EXAMPLE 1

Methyl 6α,9α- difluoro - 11β-hydroxy-16α-methyl-3-oxo-17α-propionyloxyandrosta -1,4-diene-17β-carboxylate.

A suspension of methyl 6α,9α- difluoro- 11β, 17α-dihydroxy-16α-methyl-3-oxoandrosta-1,4-diene-17β-carboxylate (394 mg.) in propionic acid (3.9 ml.) was treated, at room temperature, with trifluoroacetic anhydride (0.78 ml.) and toluene p-sulphonic acid (0.08 ml. of a dry chloroform solution concentration 0.12g. per ml.). The resulting solution was stirred at 75°-80° C for 30 mins., then added slowly to a stirred solution of 3% aqueous sodium bicarbonate (ca.250 ml). The product was extracted into ethyl acetate. The extract was washed with saturated aqueous sodium bicarbonate solution, and water, dried over magnesium sulphate, and evaporated in vacuo to give an off-white solid (466 mg.) which was purified by preparative thin layer chromatography (on silica, developing the plates three times in chloroform). A portion (156mg.) of the total purified material (356 mg.) was recrystallised twice from methanol to give the title compound (119 mg.) as white hexagonal plates, m.p. 267°-269° C(with decomposition) $[\alpha]_D + 9°$ (c 1.0 dioxan), $\lambda_{max}$ 236 nm ($\epsilon$ 16,800).

EXAMPLE 2

Chloromethyl 6α,9α-difluoro-11β-hydroxy-16β-methyl-3-oxo-17α-propionyloxyandrost-4-ene-17β-carboxylate (a) A solution of 6α,9α-difluoro-11β,17,21-trihydroxy-16β-methylpregn-4-ene-3,20-dione (0.848g.) in tetrahydrofuran (10ml) was treated with a solution of periodic acid (0.682g., $H_5IO_6$) in water (3ml.). After stirring for 2 hours, water (10ml.) was added and the solution concentrated in vacuo. Water (40ml.) was added and the product (an oil) was extracted into ethyl acetate. The combined extracts were washed with water, dried and evaporated to give 6α,9α-difluoro-11β,17β-dihydroxy-16β-methyl-3-oxoandrost-4-ene-17β-carboxylic acid as a foam [0.866g. (ethyl acetate solvate, ca 1 mole)], (b) A stirred suspension of 6α,9α-difluoro-11β,17α-dihydroxy-16β-methyl-3-oxoandrost-4-ene-17β-carboxylic acid [0.828g., (ca. 1 mole, ethyl acetate solvate)] in dry, redistilled dichloromethane (22ml.) was cooled to 0° C. and treated with redistilled triethylamine (0.96ml), then with propionyl chloride (0.63ml.), added dropwise. After stirring at ca. 0° C for 80 minutes, dichloromethane (15ml.) was added, and the solution washed with 3% aqueous sodium bicarbonate, N hydrochloric acid and water, dried (MgSO$_4$) and evaporated to give the intermediate mixed anhydride as a foam (1.02g). The foam was dissolved in acetone (33ml) and treated with diethylamine (0.75ml). After being stirred for 85 mins. solvent was evaporated, and the residue was dissolved in water (50ml.). The mixture was washed with ethyl acetate. The aqueous phase was acidified with 2N-hydrochloric acid, and the product extracted into ethyl acetate.

The combined extracts were washed with water, dried and evaporated to give 6α,9α-difluoro-11β-hydroxy-16β-methyl-3-oxo-17α-propionyloxyandrost-4-ene-17β-carboxylic acid as a solvated (ethyl acetate) foam (0.803g.), $\lambda_{max}$ 234nm ($\epsilon$ 14,990).

(c) A suspension of 6α,9α-difluoro-11β-hydroxy-16β-methyl-3-oxo-17α-propionyloxyandrost-4-ene-17β-carboxylic acid (0.754g.) in methanol (4ml.) was treated with 2M sodium hydroxide in methanol (0.9ml) to give a solution of pH 10. Ether (100ml) was added and the mixture was then refrigerated for 2 hours. The precipitate was collected by filtration, washed well with ether, then dried in vacuo to give the sodium salt (0.379g.) of the above 17β-carboxylic acid. The filtrates were evaporated, triturated with ether (50ml.) and the solid collected by filtration, washed withether, and dried in vacuo, giving more of the sodium salt (0.336.g).

The sodium salt (0.714g.) was slowly added to a stirred solution of chloroiodomethane (0.53ml., freshly redistilled b.p. 108° C) in hexamethylphosphoramide (1.8ml.). More hexamethylphosphoramide (1.8ml.) was added, after about half of the sodium salt had been added, due to a sudden gelatinous precipitation. Stirring and steroid addition were continued. After 3 hours, the mixture was diluted with ethyl acetate (100ml) and washed with water 5% aqueous sodium bicarbonate and water, dried and evaporated to a foam (0.713g.). P.L.C. (chloroform-acetone 40:1) gave two products; the major, more polar component was a foam (472mg.), a portion was crystallised twice from acetone to afford the title chloromethyl ester as solvated (acetone) colourless crystals (98mg.). m.p. 183°-184° C, $[\alpha]_D + 48.4°$ (c 0.135, dioxan), $\lambda_{max}$ 233nm ($\epsilon$ 16,570).

EXAMPLE 3

Fluoromethyl 6α,9α-difluoro-11β-hydroxy-16β-methyl-3-oxo-17α-propionyloxyandrost-4-ene-17β-carboxylate A solution of chloromethyl 6α,9α-difluoro-11β-hydroxy-16β-methyl-3-oxo-17α-propionyloxy-androst-4-ene-17β-carboxylate (0.368g.) in dry acetonitrile (5.5ml.) was stirred with silver fluoride (0.648g.) in the dark. After 7 days, the mixtured was filtered through kieselguhr, which was then washed with ethyl acetate (200ml.). The combined filtrates were washed with water, dried and evaporated to a foam (354mg.). P.L.C. (chloroform) and crystallisation twice from acetone/ether gave the solvated (ether) title compound (177mg.), m.p. 183°-184° C, $[\alpha]_D + 57.6°$ (c 0.11, dioxan), $\lambda_{max}$ 233.5nm ($\epsilon$ 15.670).

EXAMPLE 4

Methyl 6α,9α-difluoro-11β-hydroxy-16β-methyl-3-oxo-17α-propionyloxyandrost-4-ene-17β-carboxylate (a) A solution of 6β,9α-difluoro-11β,17,21-trihydroxy-16β-methylpregna-1,4-diene-3,20-dione (3.970g.) in tetrahydrofuran (40ml.) was treated with a solution of periodic acid (3.307g., $H_5IO_6$) in water (10ml.). After being stirred for 1½ hours, the solution was diluted with 5% aqueous sodium bicarbonate solution (100ml.) then concentrated in vacuo to ca. 100ml. The solution was washed with ethyl acetate, then acidified with 2N hydrochloric acid, and stirred for 45 minutes. The product was collected by filtration, washed well with water and dried in vacuo to give 6β,9α-difluoro-11β,17α-dihydroxy-16β-methyl-3-oxoandrosta-1,4-diene-17β-carboxylic acid (3.509g.).

(b) A stirred solution of 6β,9α-difluoro-11β,17α-dihydroxy-16β-methyl-3-oxoandrosta-1,4-diene-17β-carboxylic acid (3.443g.) in dry, redistilled dichloromethane (90ml.) and redistilled triethylamine (3.03ml.) was cooled to 0° C and treated with propionyl chloride (1.93ml.). After stirring at ca. 0° C. for 40 minutes, dichloromethane (60ml.) was added, and the solution washed with 3% aqueous sodium bicarbonate, N-hydrochloric acid and water, dried and evaporated to give the intermediate mixed anhydride as a foam (4.913g.). The foam was dissolved in acetone (75ml.) and treated with diethylamine (3.1ml.) After being stirred for 50 minutes, the suspension was concentrated in vacuo and dissolved in water (100ml.). The solution was acidified to pH3 with 2N hydrochloric acid and the product was extracted into ethyl acetate. The combined extracts were washed with water, dried and evaporated to a foam (4.637g.). Crystallisation from ethyl acetate gave 6β,9α-difluoro-11β-hydroxy-16β-methyl-3-oxo-17α-propionyloxyandrosta-1,4-diene-17β-carboxylic acid (2.553g). A portion (92mg.) was further crystallised from ethyl acetate to give an analytical sample as solvated (ethyl acetate) colourless crystals (89mg). m.p. 171°–174° C, $[\alpha]_D$ − 25.4° (c 1.08, dimethylsulphoxide), $\lambda_{max}$ 240nm ($\epsilon$ 16,360).

Further quantities of the 17α-propionyloxy-17β-carboxylic acid were obtained from the evaporated mother liquors, from above, by repeated extractions with 5% aqueous sodium bicarbonate and washing with ethyl acetate, acificiation and extraction with ethyl acetate. This was performed twice to give the 6β-fluoro-17α-propionyloxy-17β-carboxylic acid (0.800g., and 0.262g.).

(c) A solution of 6β,9α-difluoro-11β-hydroxy-16β-methyl-3-oxo-17α-propionyloxy-androsta-1,4-diene-17β-carboxylic acid (2.966g.) in methanol (8ml.) and benzene (200ml.) was treated with tris(triphenylphosphine)rhodium chloride (1.694g.), and stirred with hydrogen gas at room temperature and atmospheric pressure for 93 hours (uptake 262ml). The solution was concentrated in vacuo to ca. 100ml., diluted with benzene (50ml., as a wash) and extracted with 2N sodium carbonate solution. The combined extracts were washed with benzene (200ml.) then acidified to pH2 with 6N hydrochloric acid, and the products were extracted into ethyl acetate. Combined extracts were washed with water, dried and evaporated to a foam (2.923g.), containing 6β,9α-difluoro-11β-hydroxy, 16β-methyl-3-oxo-17α-propionyloxy-androst-4-ene-17β-carboxylic acid.

(d) The above prepared material (2.906g.) was dissolved in methanol, cooled to 0° C and treated with an excess of ethereal diazomethane. A few drops of acetic acid were added, and the solution was evaporated to a foam (2.985g.). This was redissolved in ethyl acetate (100ml.) and washed with 5% aqueous sodium bicarbonate and water, dried and evaporated (2.757g.). P.L.C. (chloroformacetone, 20:1) gave three components; the least polar foam (1.420g.) was methyl 6β,9α-difluoro-11β-hydroxy-16β-methyl-3-oxo-17α-propionyloxyandrost-4-ene-17β-carboxylate.

(e) A solution of methyl 6β,9α-difluoro-11β-hydroxy-16β-methyl-3-oxo-17α-propionyloxyandrost-4-ene-17β-carboxylate (1.420g.) in dioxan (18ml.) was treated with 50% w/v hydrogen bromide in acetic acid (0.22ml.). After 48 hours, the mixture was added to water (300ml.) and the product extracted with ethyl acetate. The combined extracts were washed with 5% aqueous sodium bicarbonate and water, dried and evaporated to a foam (1.410g.). P.L.C. (chloroformacetone, 14:1) gave two components; the more polar was the title 6α-fluoro ester (0.365g.), the less polar was unchanged 6 β-fluoro ester (0.974g.).

The latter material was redissolved in dioxan (12ml.) and treated with 50% w/v hydrogen bromide in acetic acid (0.15ml.). After 66 hours a similar isolation of product, followed by P.L.C. (chloroform-acetone, 16:1) gave two components; the more polar was the title 6α-fluoro ester (0.557g.).

The two batches (0.365g. and 0.557g) were combined and crystallised twice from methanol to give the analytical sample (0.423g.), m.p. 195°–197° C, $[\alpha]_D$ + 44° (c 0.17, dioxan), $\lambda_{max}$ 233.5nm ($\epsilon$ 15,730).

EXAMPLE 5

Methyl 6α,9α-difluoro-11β-hydroxy-16β-methyl-3-oxo-17α-propionyloxyandrosta-1,4-diene-17β-carboxylate A solution of methyl 6α,9α-difluoro-11β-hydroxy-16β-methyl-3-oxo-17α-propionyloxyandrost-4-ene-17β-carboxylate (0.657g.) and 2,3-dichloro-5,6-dicyanobenzoquinone (0.546g.) in benzene (50ml) was heated under reflux for 7 days. The solvent was evaporated, and the mixture was purified by P.L.C. (chloroform/acetone, 20:1). The major steroid product was a foam (0.413g.). Crystallisation (3×) from methanol gave the title compound (0.273g.) m.p. 236°–238° C. $[\alpha]_D$ + 31.6° (c 0.1 dioxan), $\lambda_{max}$ 237.5nm ($\epsilon$ 16,200).

PREPARATION 1

21-Acetoxy-3-benzoyloxy-9α-fluoro-11β,17α-dihydroxy-16β-methyl pregna-1,3,5-trien-20-one Redistilled benzoyl chloride (340ml.) was added to a solution of betamethasone acetate (134g.) in pyridine (550ml.), cooled in an ice-bath, and the mixture was then heated at 50°, in a thermostatically controlled bath, for 2 hr. The cooled suspension was poured into an excess of saturated aqueous sodium hydrogen carbonate and the product was extracted into ethyl acetate. The extract was washed with 2N-hydrochloric acid, aqueous sodium hydrogen carbonate, and water, and dried (MgSO$_4$). The extract was concentrated in vacuo and the crystals of the enol benzoate which separated (57.9g.) m.p. 124°–126°, $[\alpha]_D$ − 138° (c, 1.0 in CHCl$_3$) were collected and washed with ether.

Recrystallisation of a sample of the enol benzoate from benzene - ether gave an analytical sample of the title compound m.p. 124°, $[\alpha]_D$ − 144° (CHCl$_3$), $\lambda_{max}$ 230nm, ($\epsilon$ 20,200) and 309nm ($\epsilon$ 6,880).

PREPARATION 2

6β-Fluorobetamethasone 21-acetate (21-Acetoxy-6β,9α-difluoro-11β,17α-dihydroxy-16β-methylpregna-1,4-diene-3,20-dione)

Perchloryl fluoride (ca 25 g., = ca. 14 ml. at −70°) was passed slowly in a nitrogen stream, into a solution of 21-acetoxy-3-benzoyloxy-9α-fluoro-11β,17α-dihydroxy-16β-methylpregna-1,3,5(10)-trien-20-one (117g.) in pyridine (400ml., previously distilled from selenium dioxide) kept at 5°. The reaction flask was fitted with a cold finger condenser at −70° and the excess of perchloryl fluoride was kept refluxing from the stirred suspension for 1 hr. The excess of reagent was removed with a vigorous stream of nitrogen and the mixture was poured into ice-water and carefully neutralised with hydrochloric acid. The precipitate was collected by filtration and dried at room temperature in air.

Part (90%) of the crude solid was suspended in ethyl acetate (500ml.) and water (200ml.) containing sodium metabisulphite (30g.) and then acetic acid (15ml.) was added. The mixture was shaken until all the steroid dissolved and the organic layer was then separated, washed with aqueous sodium hydrogen carbonate and water, and dried (MgSO₄). Removal of the solvent in vacuo left a residue, which was partly-dissolved by warm chloroform. After separation of the insoluble material (5.3g.), the chloroform was evaporated to dryness and the resultant foam was crystallised from ethyl acetate to give 6β-fluorobetamethasone 21-acetate as a solvate (41.3 g.), m.p. 111°–112°, λmax. 239nm.($E_{1cm}^{1\%}$, 292,) $[α]_D + 41°$ (CHCl₃). After drying at 150° in vacuo it had m.p. 130° and analysed approximately for a solvate with one molecule of ethyl acetate.

PREPARATION 3

6β,9α-Difluoro-11β,17,21-trihydroxy-16β-methylpregna-1,4-diene-3,20-dione

A solution of 6β-fluoro-betamethasone 21-acetate (6.184g.) in methanol (130ml.) and dioxan (130ml.) was treated with a solution of potassium carbonate (1.651g.) in water (10ml.). The mixture was stirred for 80 mins, acidified to pH 5 with acetic acid, then concentrated in vacuo to ca. 100ml. Water (700ml.) was added, and the mixture stirred in ice for 1 hour. The solid was collected by filtration washed well with water and dried in vacuo to give the title compound (3.998g.)

The following Examples illustrate pharmaceutical compositions according to the invention.

Example A: Water-miscible cream

| Active ingredient | 0.1% w/w |
| Beeswax (White) | 15.0% w/w |
| Cetostearyl alcohol B.P.C. | 7.0% w/w |
| Cetomacrogol 1000 B.P.C. | 3.0% w/w |
| Liquid paraffin B.P. | 5.0% w/w |
| Chlorocresol | 0.1% w/w |
| Distilled water to produce | 100 parts by weight |

Ball-mill the steroid with a little liquid paraffin until the particle size is reduced to 95% by number below 5μ. Heat the available water to 100° C, add the chlorocresol, stir to dissolve and cool to 65° C. Melt together the beeswax, cetostearyl alcohol and cetomacrogol and maintain at 65° C. Add the steroid suspension using the remaining liquid paraffin for rinsing. Add the steroid oil phase at 60° C to the chlorocresol aqueous phase at 65° C and stir rapidly while the emulsion cools over the gelling point (40°–45° C). Continue to stir at slow speed until the cream sets.

Example B: Oral tablet

| Active ingredient | 0.5 mg. |
| Lactose | 175.5 mg. |
| Maize starch (dried) | 20.0 mg. |
| Gelatin | 2.0 mg. |
| Magnesium stearate | 2.0 mg. |
| Tween 80 | Trace |
| Total weight | 200.0 mg. |

A suspension of 300mg. of the active ingredient in 2ml. of water containing 0.1% of Tween 80 is milled for 16 hours in a 10ml. nylon pot about three quarters filled with steatite balls, until 90% by number of the particles have a diameter of less than 5 microns with none greater than 50 microns. The maize starch and lactose are blended and passed through a 60 mesh B.S. sieve and granulated with a 10% solution of gelatin containing the suspension of the active ingredient and washings from the nylon pot, by passing through a 16 mesh B.S. sieve. The granules are dried at 40° C overnight, passed through a 20 mesh B.S. sieve and blended with magnesium stearate and tabletted using a tabletting machine having a 5/16 inch flat-bevelled punch.

We claim:

1. Compounds of the general formula

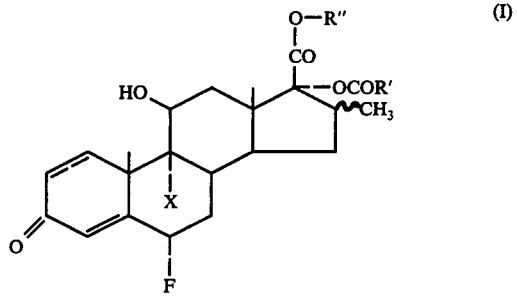

wherein X represents a hydrogen or fluorine atom, R' represents a methyl, ethyl, n-propyl or iso-propyl group, R" represents a methyl, chloromethyl, fluoromethyl, bromomethyl or 2- fluoroethyl group and $=\!=$ represents a single or double bond.

2. Compounds as claimed in claim 1 wherein R' represents an ethyl group.

3. Compounds as claimed in claim 1 wherein R" represents a methyl, chloromethyl or fluoromethyl group.

4. A compound as claimed in claim 1, said compound being methyl 6α,9α-difluoro-11β-hydroxy-16α-methyl-3-oxo-17α-propionyloxy androsta-1,4diene-17β-carboxylate.

5. A compound as claimed in claim 1, said compound being fluoromethyl 6α,9α-difluoro-11β-hydroxy-16β-methyl-3-oxo-17α-propionyloxyandrost-4-ene-17β-carboxylate.

6. A compound as claimed in claim 1 selected from chloromethyl 6α,9α-difluoro-11β-hydroxy-16β-methyl-3-oxo-17α-propionyloxyandrost-4-ene-17β-carboxylate; methyl 6α,9α-difluoro-11β-hydroxy-16β-methyl-3-oxo-17α-propionyloxy-androsta-1,4-diene-17β-carboxylate; and methyl 6α,9α-difluoro-11β-hydroxy-16β-methyl-3-oxo-17α-propionyloxy-androst-4-ene-17β-carboxylate.

7. Pharmaceutical compositions comprising, as active ingredient, at least one compound of claim 1 together with at least one pharmaceutical carrier or excipient.

8. Compounds as claimed in claim 3 wherein X is a fluorine atom.

9. A compound as claimed in claim 1 which is methyl 6α,9α-difluoro-11β-hydroxy-16β-methyl-3-oxo-17α-propionyloxyandrost-4-ene-17β-carboxylate.

10. A composition as claimed in claim 7 adapted for topical administration comprising at least one topical carrier or excipient, wherein the compound is present in an amount in the range of from 0.0001 to 5.0 percent by weight.

11. The compound of claim 3 wherein the 16-methyl group is in the alpha configuration.

12. A compound as claimed in claim 1 which is chloromethyl 6α,9α-difluoro-11β-hydroxy-16β-methyl-3-oxo-17α-propionyloxyandrost-4-ene-17β-carboxylate.

13. A method of treating inflammation which comprises topically applying to the skin a composition as set forth in claim 10.

* * * * *